(12) United States Patent
Takagi

(10) Patent No.: US 11,467,144 B2
(45) Date of Patent: Oct. 11, 2022

(54) LIGHT EMITTING AND RECEIVING APPARATUS AND METHOD OF DIAGNOSING DETERIORATION

(71) Applicant: Asahi Kasei Microdevices Corporation, Tokyo (JP)

(72) Inventor: Yuta Takagi, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 349 days.

(21) Appl. No.: 16/828,957

(22) Filed: Mar. 25, 2020

(65) Prior Publication Data

US 2020/0309752 A1    Oct. 1, 2020

(30) Foreign Application Priority Data

Mar. 25, 2019 (JP) .............................. JP2019-056808
Mar. 16, 2020 (JP) .............................. JP2020-045148

(51) Int. Cl.
*G01N 33/00*  (2006.01)
*G01N 21/3504*  (2014.01)

(52) U.S. Cl.
CPC ..... *G01N 33/0006* (2013.01); *G01N 21/3504* (2013.01); *G01N 33/004* (2013.01)

(58) Field of Classification Search
CPC ........... G01N 33/0006; G01N 21/3504; G01N 33/004; G01N 2021/399; G01N 2201/062; G01N 21/274
See application file for complete search history.

(56) References Cited

U.S. PATENT DOCUMENTS

| 9,332,598 | B1 * | 5/2016 | Ho | .................. H05B 45/375 |
| 2013/0145330 | A1 * | 6/2013 | Choi | ................. H01L 27/14601 716/107 |
| 2016/0066383 | A1 * | 3/2016 | Dias | .................. H05B 45/14 315/297 |
| 2019/0056329 | A1 * | 2/2019 | Low | .................. G01N 21/75 |

FOREIGN PATENT DOCUMENTS

| JP | 2006046940 A | 2/2006 | |
| WO | WO-2014129729 A1 * | 8/2014 | ............ G01J 1/0418 |

* cited by examiner

*Primary Examiner* — David P Porta
*Assistant Examiner* — Mamadou Faye
(74) *Attorney, Agent, or Firm* — Kenja IP Law PC

(57) ABSTRACT

A light emitting and receiving apparatus includes a controller and a calculator. The controller acquires a first detection current from a light-receiving element when supplying a first drive current to a light-emitting element and acquires a second detection current from the light-receiving element when supplying a second drive current to the light-emitting element. The calculator generates a signal indicating deterioration of the light-emitting element when a reference value and an aging value satisfy a deterioration judgment condition, the aging value being a ratio between the first detection current and the second detection current. The detection accuracy of the light emitting and receiving apparatus is thereby improved.

15 Claims, 5 Drawing Sheets

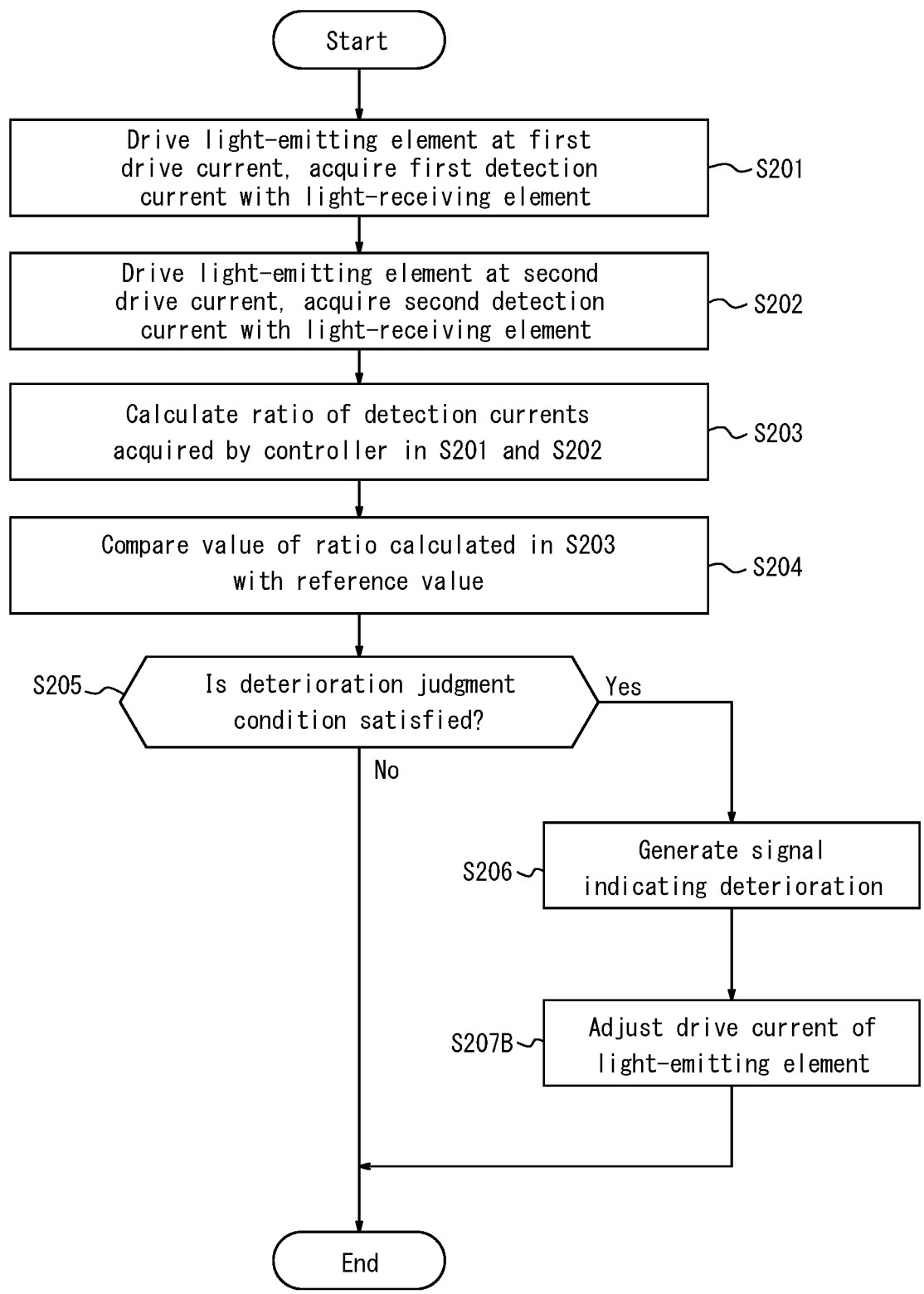

LIGHT EMITTING AND RECEIVING APPARATUS AND METHOD OF DIAGNOSING DETERIORATION

TECHNICAL FIELD

The present disclosure relates to a light emitting and receiving apparatus and a method of diagnosing deterioration.

BACKGROUND

A known gas detection apparatus includes a light-emitting element that emits infrared light and a light-receiving element that receives infrared light that has passed through a target gas (such as $CO_2$ gas). The gas detection apparatus can measure the concentration of the gas that absorb infrared light. The gas detection apparatus is calibrated at predetermined periods set in advance (such weekly or yearly) considering factors such as deterioration over time of the light-emitting element.

Patent literature (PTL) 1, for example, discloses an optical recording medium detection system that periodically corrects the drive current of a light-emitting element on daily calibration. The amount of light irradiated onto a light-receiving unit is maintained at the predetermined value set at initial calibration.

CITATION LIST

Patent Literature

PTL 1: JP2006-46940A

SUMMARY

It was difficult, however, to diagnose the deterioration of a light-emitting element easily and accurately in a known light emitting and receiving apparatus. Therefore, it has been necessary to judge the deterioration of the light-emitting element based on characteristics other than light, such as a forward voltage of the light-emitting element when a drive current inputs to the light-emitting element and a reverse current of the light-emitting element when a reverse voltage applies to the light source. But these characteristics have temperature-dependency. These temperature dependencies make the diagnosing of deterioration complicated and difficult. It is not suitable for diagnosing easily and accurately.

One possible calibration method would be to predict degradation from the driving period and then calibrate, as in a calibration method for regular, yearly calibration. Since the degree of degradation varies in each device and depends on the environment of usage, however, calibration might not be performed when necessary with this method. Therefore, the detection accuracy of the light emitting and receiving apparatus may be inaccurate.

The present disclosure therefore aims to improve the detection accuracy of a light emitting and receiving apparatus.

A light emitting and receiving apparatus according to the present disclosure includes a light-emitting element configured to output light of an amount corresponding to a drive current, a light-receiving element configured to receive light from the light-emitting element and output a detection current corresponding to an amount of received light, a controller configured to supply the drive current to the light-emitting element and acquire the detection current from the light-receiving element, and a calculator. The controller is configured to acquire a first detection current from the light-receiving element when supplying a first drive current to the light-emitting element and acquire a second detection current from the light-receiving element when supplying a second drive current to the light-emitting element. The calculator is configured to generate a signal indicating deterioration of the light-emitting element when a reference value and an aging value satisfy a deterioration judgment condition, the age value being a ratio between the first detection current and the second detection current.

A method according to the present disclosure is a method of diagnosing deterioration of a light-emitting element, the method being performed by a light emitting and receiving apparatus including a light-emitting element configured to output light of an amount corresponding to a drive current and a light-receiving element configured to receive light from the light-emitting element and output a detection current corresponding to an amount of received light. The method includes supplying the drive current to the light-emitting element and acquiring the detection current from the light-receiving element, acquiring a first detection current from the light-receiving element when a first drive current is supplied to the light-emitting element, acquiring a second detection current from the light-receiving element when a second drive current is supplied to the light-emitting element, and generating a signal indicating deterioration of the light-emitting element when a reference value and an aging value satisfy a deterioration judgment condition, the age value being a ratio between the first detection current and the second detection current.

The present disclosure can improve the detection accuracy of a light emitting and receiving apparatus.

BRIEF DESCRIPTION OF THE DRAWINGS

In the accompanying drawings:

FIG. 5 is a flowchart illustrating an example of a method of diagnosing deterioration according to a third modification.

DETAILED DESCRIPTION

Embodiments of the present disclosure are described in detail below with reference to the drawings.

<Configuration of Light Emitting and Receiving Apparatus>

Figure 1:
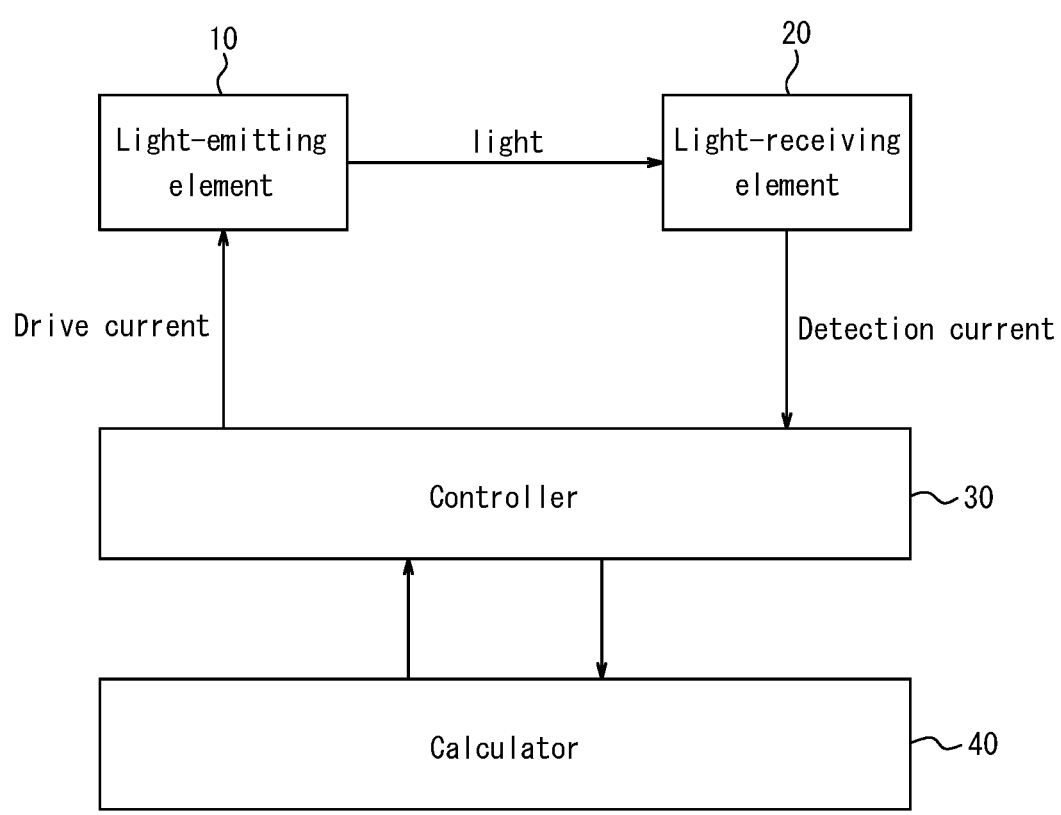
FIG. 1 illustrates an example of the configuration of a light emitting and receiving apparatus according to the present embodiment.

A light emitting and receiving apparatus 100 according to the present embodiment is now described with reference to FIG. 1. FIG. 1 illustrates an example of the configuration of the light emitting and receiving apparatus 100 according to the present embodiment.

As illustrated in FIG. 1, the light emitting and receiving apparatus 100 includes a light-emitting element 10, a light-receiving element 20, a controller 30, and a calculator 40.

The light-emitting element 10 emits light in accordance with a drive current supplied from the controller 30. The light-emitting element 10 emits light with a wavelength longer than 0.7 µm, for example. When the light emitting and receiving apparatus 100 is a gas detection apparatus, for example, the predetermined light is preferably light of a wavelength region that includes a wavelength absorbed by a gas to be detected, such as $CO_2$ gas. This wavelength region may, for example, be near 4.3 µm.

The light-emitting element 10 is, for example, a light-emitting diode (LED), a semiconductor laser, a micro electro mechanical systems (MEMS) heater, or the like. The light-emitting element 10 is particularly preferably an LED.

The reason why the deterioration rate of the light-emitting element 10 depends on the drive current supplied to the light-emitting element 10 is now described briefly. Degradation of the light-emitting element 10 is thought to depend on a reduction in the internal quantum efficiency due to crystal defects. The internal quantum efficiency $\eta_{IRQ}$ is proportional to Expression (1) below.

$$\eta_{IRQ} \propto \frac{Bn^2}{An + Bn^2 + Cn^3} \quad (1)$$

In Expression (1), A represents the Shockley-Read-Hall (SRH) recombination coefficient, B represents the light-emission recombination coefficient, C represents the Auger recombination coefficient, and n represents the carrier density.

Since A is most affected by crystal defects, it is clear from Expression (1) that the internal quantum efficiency is dependent on the drive current supplied to the light-emitting element 10. In other words, it is clear that the deterioration rate of the light-emitting element 10 depends on the drive current supplied to the light-emitting element 10.

The light-receiving element 20 receives at least a portion of the predetermined light emitted by the light-emitting element 10 and outputs a detection current corresponding to the amount of received light to the controller 30. For example, the light-receiving element 20 receives at least a portion of light in a wavelength region including a wavelength longer than 0.7 µm and outputs a detection current corresponding to the amount of received light to the controller 30. When the light emitting and receiving apparatus 100 is a gas detection apparatus, for example, the light-receiving element 20 may be configured to be capable of receiving light of a wavelength region that includes a wavelength absorbed by a gas to be detected, such as $CO_2$ gas. This wavelength region may, for example, be near 4.3 µm.

The light-receiving element 20 is, for example, a quantum sensor, a quantum infrared sensor, a thermal infrared sensor, or the like. Examples of a quantum infrared sensor include a phototube, a photodiode, and a phototransistor. Examples of a thermal infrared sensor include a pyroelectric sensor, a thermopile, and a bolometer.

The light-receiving element 20 may be formed on the same substrate as the light-emitting element 10. When the light-receiving element 20 and the light-emitting element 10 are formed on the same substrate, separate substrates need not be prepared, which can reduce manufacturing costs.

The light-receiving element 20 may further include an optical filter that has the function of transmitting a certain wavelength of light. Examples of the optical filter include a bandpass filter that transmits light in a wavelength region near 4.3 µm.

The controller 30 supplies drive current to the light-emitting element 10 and acquires a detection current from the light-receiving element 20. The controller 30 also converts the detection current acquired from the light-receiving element 20 to a signal which is able to be processed by the calculator 40. The controller 30 is, for example, an analog front end (AFE). The AFE may be configured by a single AFE circuit or a combination of a plurality of AFE circuits.

The controller 30 supplies two types of drive currents with different values (the first drive current and second drive current described below), for example, to the light-emitting element 10. As described above, the deterioration rate of the light-emitting element, as the deterioration affects the internal quantum efficiency, 10 depends on the drive current supplied to the light-emitting element 10. Accordingly, by the controller 30 supplying two types of drive currents with different values to the light-emitting element 10, the calculator 40 can judge the deterioration state of the light-emitting element 10 based on the ratio of the deterioration rates of the light-emitting element 10. The calculator 40 can also generate a signal indicating deterioration based on a deterioration judgment condition, described below. Instead of only two types of drive currents with different values, the controller 30 can also supply a plurality of types of drive currents with different values to the light-emitting element 10.

When the controller 30 supplies the first drive current to the light-emitting element 10 at a predetermined timing, for example, the controller 30 acquires a first detection current from the light-receiving element 20. When the controller 30 supplies the second drive current to the light-emitting element 10 at a predetermined timing, for example, the controller 30 acquires a second detection current from the light-receiving element 20. The predetermined timing is the time when the calculator 40 calculates a reference value for an aging value, described below.

A first detection current $I_{p1}$ at the predetermined timing can be represented by Expression (2) below.

$$I_{p1} = \Phi_{p1}(I_2) * R_\lambda * T_x * T_{abs} \quad (2)$$

A second detection current $I_{p2}$ at the predetermined timing can be represented by Expression (3) below.

$$I_{p2} = \Phi_{p2}(I_2) * R_\lambda * T_x * T_{abs} \quad (3)$$

$I_1$ represents the first drive current supplied to the light-emitting element 10. $I_2$ represents the second drive current supplied to the light-emitting element 10. $\Phi_{p1}$ represents the amount of light emitted by the light-emitting element 10 with respect to the first drive current $I_1$. $\Phi_{p2}$ represents the amount of light emitted by the light-emitting element 10 with respect to the second drive current $I_2$. $R_\lambda$ represents the sensitivity of the sensor. $T_x$ represents the light guiding efficiency assuming that a light guiding mechanism (such as a light guide) is included. $T_{abs}$ represents the light decay rate due to gas.

The controller 30 acquires the first detection current $I_{p1}$ and the second detection current $I_{p2}$ substantially simultaneously. For example, the controller 30 acquires the first detection current $I_{p1}$ and the second detection current $I_{p2}$ so that the interval between the acquisition time of the first detection current $I_{p1}$ and the acquisition time of the second detection current $I_{p2}$ is 10 seconds or less. The controller 30 can thereby acquire the first detection current $I_{p1}$ and the second detection current $I_{p2}$ while the temperature of the light-emitting element 10 does not significantly change. This enables the calculator 40 to accurately calculate a value necessary for determining the timing of calibration (a comparison between the reference value and the aging value, described below).

By the controller 30 acquiring the first detection current $I_{p1}$ and the second detection current $I_{p2}$ substantially simultaneously, the calculator 40 can calculate the ratio between these currents (the reference value described below) without taking into account values such as the light transmission efficiency, the light decay rate due to gas, and the decay of reflectance of the gas cell. Accordingly, the calculator 40 can easily and accurately calculate the value necessary for determining the timing of calibration. In a measurement environment in which the temperature of the light-emitting element 10 rises rapidly over a very short time, the controller 30 may first acquire the first detection current $I_{p1}$ and then acquire the second detection current $I_{p2}$ after the measurement environment stabilizes.

When the controller 30 supplies the first drive current to the light-emitting element 10 after a predetermined length of time has elapsed from the predetermined timing, for example, the controller 30 acquires the first detection current from the light-receiving element 20. When the controller 30 supplies the second drive current to the light-emitting element 10 after the predetermined length of time has elapsed from the predetermined timing, for example, the controller 30 acquires the second detection current from the light-receiving element 20.

A first detection current $I'_{p1}$ after a predetermined period has elapsed from the predetermined timing can be represented by Expression (4) below.

$$I'_{p1} = \alpha_1 * \Phi_{p1}(I_1) * R_\lambda * T'_x * T'_{abs} \quad (4)$$

A second detection current $I'_{p2}$ after a predetermined period has elapsed from the predetermined timing can be represented by Expression (5) below.

$$I'_{p2} = \alpha_2 * \Phi_{p1}(I_1) * R_\lambda * T'_x * T'_{abs} \quad (5)$$

$I_1$ represents the first drive current supplied to the light-emitting element 10. $I_2$ represents the second drive current supplied to the light-emitting element 10. $\alpha_1$ represents the deterioration rate from the predetermined timing when the first drive current is supplied to the light-emitting element 10. $\alpha_2$ represents the deterioration rate from the predetermined timing when the second drive current is supplied to the light-emitting element 10. $\alpha_1 * \Phi_{p1}$ represents the amount of light emitted by the light-emitting element 10 with respect to the first drive current $I_1$, and $\alpha_2 * \Phi_{p2}$ represents the amount of light emitted by the light-emitting element 10 with respect to the second drive current $I_2$. $R_\lambda$ represents the sensitivity of the sensor. $T'_x$ represents the light transmission efficiency assuming that a light guiding mechanism (such as a light guide) is included. $T'_{abs}$ represents the light decay rate due to gas.

As when acquiring the first detection current $I_{p1}$ and the second detection current $I_{p2}$, the controller 30 acquires the first detection current $I'_{p1}$ and the second detection current $I'_{p2}$ substantially simultaneously. For example, the controller 30 acquires the first detection current $I'_{p1}$ and the second detection current $I'_{p2}$ substantially simultaneously so that the interval between the acquisition time of the first detection current $I'_{p1}$ and the acquisition time of the second detection current $I'_{p2}$ is 10 seconds or less. The controller 30 can thereby acquire the first detection current $I'_{p1}$ and the second detection current $I'_{p2}$ while the temperature of the light-emitting element 10 does not significantly change. This enables the calculator 40 to accurately calculate a value necessary for determining the timing of calibration.

By the controller 30 acquiring the first detection current $I'_{p1}$ and the second detection current $I'_{p2}$ substantially simultaneously, the calculator 40 can calculate the ratio between these currents (the aging value described below) without taking into account values such as the light transmission efficiency, the light decay rate due to gas, and the decay of reflectance of the gas cell. Accordingly, the calculator 40 can easily and accurately calculate the value necessary for determining the timing of calibration.

The calculator 40 includes a CPU, memory, and the like, for example, and controls operations of each component included in the light emitting and receiving apparatus 100. The calculator 40 implements various processes by executing a predetermined program or the like loaded in memory.

The calculator 40 calculates a reference value S that is the ratio between the first detection current $I_{p1}$ acquired by the controller 30 at a predetermined timing and the second detection current $I_{p2}$ acquired by the controller 30 at the predetermined timing.

The reference value S can be represented by Expression (6) below, based on Expressions (2) and (3).

$$S = \frac{I_{p1}}{I_{p2}} = \frac{\Phi_{p1}}{\Phi_{p2}} \quad (6)$$

The calculator 40 calculates an aging value P that is the ratio between the first detection current $I'_{p1}$ acquired by the controller 30 after the predetermined length of time has elapsed from the predetermined timing and the second detection current $I'_{p2}$ acquired by the controller 30 after the predetermined period has elapsed from the predetermined timing.

The aging value P can be represented by Expression (7) below, based on Expressions (4) and (5).

$$P = \frac{I'_{p1}}{I'_{p2}} = \frac{\alpha_1}{\alpha_2} * \frac{\Phi_{p1}}{\Phi_{p2}} \quad (7)$$

The calculator 40 calculates the ratio between the reference value S and the aging value P based on Expressions (6) and (7). The ratio between the reference value S and the aging value P (for example, aging value P/reference value S) can be represented by Expression (8) below based on Expressions (6) and (7).

$$P = \frac{I'_{p1}}{I'_{p2}} = \frac{\alpha_1}{\alpha_2} * \frac{I_{p1}}{I_{p2}} = \frac{\alpha_1}{\alpha_2} * S \quad (8)$$

$$\therefore \frac{P}{S} = \frac{\alpha_1}{\alpha_2}$$

As described above, the reference value S is the ratio between the first detection current $I_{p1}$ and the second detection current $I_{p2}$ at a predetermined timing (such as time $t_N$). The aging value P is the ratio between the first detection current $I'_{p1}$ and the second detection current $I'_{p2}$ after a predetermined period has elapsed from a predetermined timing (for example, at time $t_{N+1}$). The reference value S is not necessarily calculated by the calculator 40. The reference value S, for example, may instead be a certain value set in the controller 30 in advance.

The calculator 40 judges whether the ratio between the reference value S and the aging value P is greater than a threshold (first threshold) $T_1$. The threshold $T_1$ is, for example, set to be the result of dividing the deterioration rate $\alpha_1$ from the predetermined timing when the first drive current is supplied to the light-emitting element 10 by the deterioration rate $\alpha_2$ from the predetermined timing when the second drive current is supplied to the light-emitting element 10, i.e. $\alpha_1/\alpha_2$. The calculator 40 compares the ratio between the reference value S and the aging value P to the threshold $T_1$ to judge whether a deterioration judgment condition $J_1$ is satisfied. Here, the deterioration judgment condition $J_1$ is the condition of the ratio between the reference value S and the aging value P being greater than the threshold $T_1$.

When the deterioration judgment condition $J_1$ is satisfied, the calculator 40 generates a signal indicating deterioration. Conversely, when the deterioration judgment condition $J_1$ is not satisfied, the calculator 40 does not generate a signal indicating deterioration. The ratio between the reference value S and the aging value P changes as deterioration of the light-emitting element 10 progresses. Therefore, by the calculator 40 generating a signal indicating deterioration at the time when the deterioration judgment condition $J_1$ is satisfied, the light emitting and receiving apparatus 100 can request calibration at an appropriate timing.

Alternatively, the calculator 40 may judge whether the ratio between the reference value S and the aging value P is equal to or less than a threshold (second threshold) $T_2$. The threshold $T_2$ is, for example, set to be the result of dividing the deterioration rate $\alpha_2$ from the predetermined timing when the second drive current is supplied to the light-emitting element 10 by the deterioration rate $\alpha_1$ from the predetermined timing when the first drive current is supplied to the light-emitting element 10, i.e. $\alpha_2/\alpha_1$. The calculator 40 compares the ratio between the reference value S and the aging value P to the threshold $T_2$ to judge whether a deterioration judgment condition $J_2$ is satisfied. Here, the deterioration judgment condition $J_2$ is the condition of the ratio between the reference value S and the aging value P being equal to or less than the threshold $T_2$.

When the deterioration judgment condition $J_2$ is satisfied, the calculator 40 generates a signal indicating deterioration. Conversely, when the deterioration judgment condition $J_2$ is not satisfied, the calculator 40 does not generate a signal indicating deterioration. The ratio between the reference value S and the aging value P changes as deterioration of the light-emitting element 10 progresses. Therefore, by the calculator 40 generating a signal indicating deterioration at the time when the deterioration judgment condition $J_2$ is satisfied, the light emitting and receiving apparatus 100 can request calibration at an appropriate timing.

The thresholds are not limited to the above-described threshold $T_1$ and threshold $T_2$ and may be set freely by the user. The number of thresholds is not restricted, either. Any number of thresholds, one or more, may be set. When two thresholds are set (first threshold, second threshold), for example, the deterioration judgment condition can be that the ratio between the reference value S and the aging value P be equal to or greater than the first threshold and equal to or less than the second threshold.

The light emitting and receiving apparatus 100 may further include a storage 50. The storage 50 may be any component having the function of storing various information, such as a DRAM, HDD, or the like. For example, the storage 50 stores the first detection current $I_{p1}$ acquired by the controller 30 at the predetermined timing, the second detection current $I_{p2}$ acquired by the controller 30 at the predetermined timing, the reference value S that is the ratio between the first detection current $I_{p1}$ acquired by the controller 30 at the predetermined timing and the second detection current $I_{p2}$ acquired by the controller 30 at the predetermined timing, the first detection current $I'_{p1}$ acquired by the controller 30 after the predetermined period has elapsed from the predetermined timing, the second detection current $I'_{p2}$ acquired by the controller 30 after the predetermined period has elapsed from the predetermined timing, the aging value P that is the ratio between the first detection current $I'_{p1}$ acquired by the controller 30 after the predetermined period has elapsed from the predetermined timing and the second detection current $I'_{p2}$ acquired by the controller 30 after the predetermined period has elapsed from the predetermined timing, various programs and information necessary for the calculator 40 to execute various processes, and the like. The storage 50 may be provided inside the calculator 40.

Instead of storing just one of each of the first detection current $I_{p1}$, the second detection current $I_{p2}$, the reference value S, the first detection current $I'_{p1}$, the second detection current $I'_{p2}$, the aging value P, and the like, the storage 50 may store a plurality of each of these values.

The light emitting and receiving apparatus 100 may further include a communication interface 60. For example, the communication interface 60 can communicate with an external apparatus in a wired or wireless manner and transmit a signal requesting calibration of the light emitting and receiving apparatus 100 to the external apparatus based on an instruction signal inputted from the calculator 40. The user who operates the external apparatus can thereby recognize the need for calibration of the light emitting and receiving apparatus 100. Alternatively, the communication interface 60 may transmit a signal requesting calibration to the light emitting and receiving apparatus 100 itself so that self-calibration can be performed. In either case, calibration of the light emitting and receiving apparatus 100 can be performed at an appropriate timing.

The communication interface 60 can transmit not only the calibration request signal but also various data inputted from the calculator 40 and information stored in the storage 50 to the external apparatus. On the basis of the data, the external apparatus can also cause a display to display predetermined information such as measurement results or the time calibration was performed.

A universal asynchronous receiver transmitter (UART) interface, for example, may be used in the communication interface 60. The communication interface 60 may, for example, be implemented via one or more of the following; an external memory interface, a universal asynchronous receiver/transmitter (UART) interface, an enhanced serial peripheral interface (eSPI), a general-purpose input/output interface, a pulse code modification (PCM) and/or inter-IC sound (I2S) interface, an inter-integrated circuit (I2C) bus interface, a universal serial bus (USB) interface, a Bluetooth interface, a ZigBee interface, an Infrared Data Association (IrDA) interface, and a wireless universal serial bus (W-USB) interface. The communication interface 60 is not limited to being implemented in these ways.

The light emitting and receiving apparatus 100 according to the present embodiment supplies two types of drive currents with different values to the light-emitting element 10 and uses the change in the ratio between the reference value S and the aging value P to determine the timing of calibration. Consequently, calibration is performed at an appropriate timing in all environments, which makes the detection accuracy of the light emitting and receiving apparatus 100 improved.

<Method of Diagnosing Deterioration>

Figure 2:
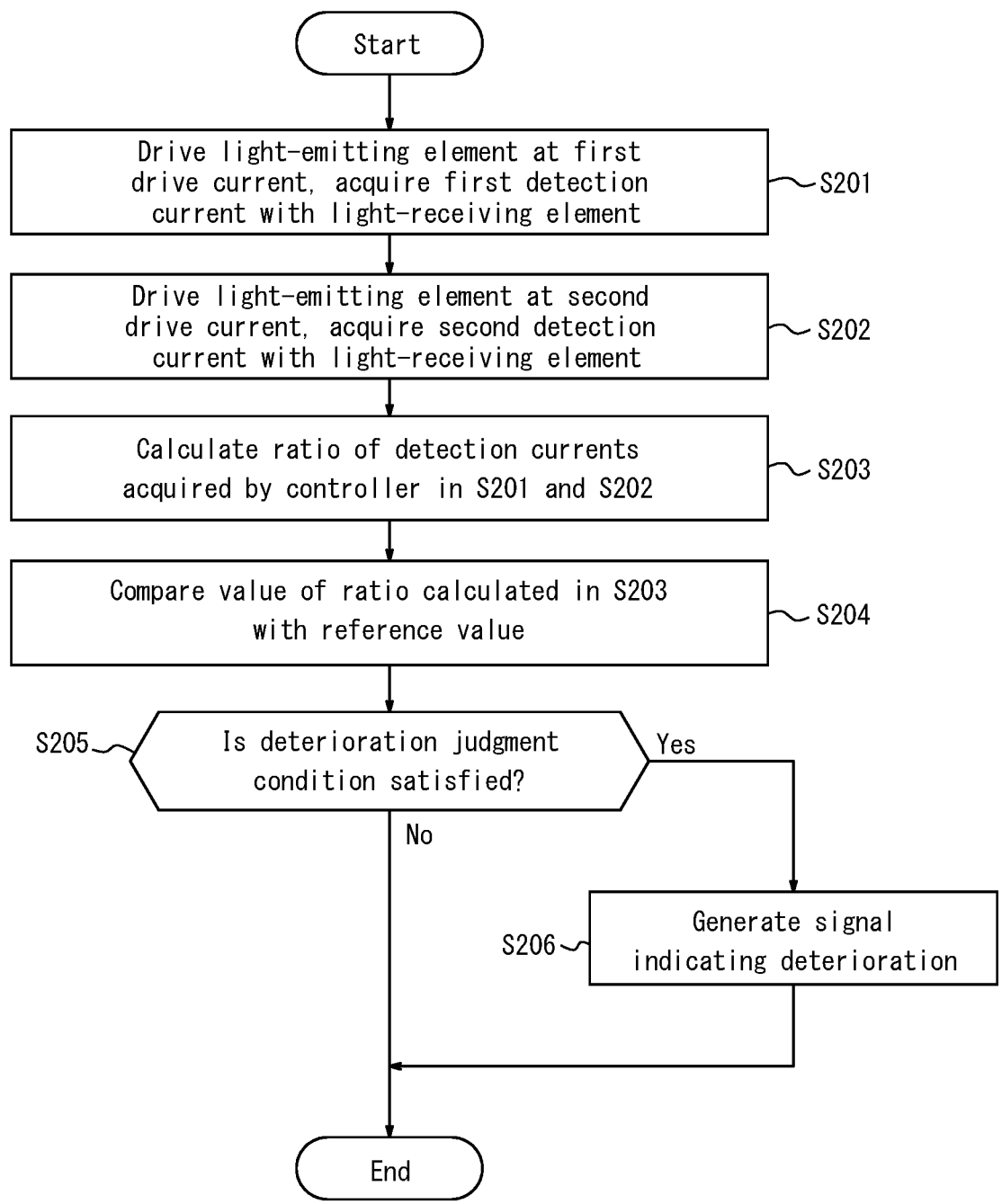
FIG. 2 is a flowchart illustrating an example of a method of diagnosing deterioration according to the present embodiment.

A method of diagnosing deterioration according to the present embodiment is now described with reference to FIG. 2. FIG. 2 is a flowchart illustrating an example of a method of diagnosing deterioration.

In step S201, the controller 30 drives the light-emitting element 10 at the first drive current and acquires the first detection current from the light-receiving element 20.

In step S202, the controller 30 drives the light-emitting element 10 at the second drive current and acquires the second detection current from the light-receiving element 20.

In step S203, the calculator 40 calculates the aging value, which is the ratio between the first detection current acquired in step S201 and the second detection current acquired in step S202.

In step S204, the calculator 40 calculates the ratio between a reference value and the aging value calculated in step S203 and compares this ratio with the threshold T. The threshold T is a predetermined value set by the user.

In step S205, the calculator 40 judges whether the ratio between the reference value and the aging value is greater than the threshold T, i.e. whether the deterioration judgment condition is satisfied. When the calculator 40 judges that the ratio between the reference value and the aging value is greater than the threshold T, i.e. that the deterioration judgment condition is satisfied, the process proceeds to step S206. When the calculator 40 judges that the ratio between the reference value and the aging value is equal to or less than the threshold T, i.e. that the deterioration judgment condition is not satisfied, the process terminates.

In step S206, the calculator 40 generates a signal indicating deterioration. And the calculator 40 may outputs an instruction signal to the communication interface 60.

The above-described method of diagnosing deterioration can easily and accurately diagnose the deterioration of a light-emitting element. The knowledge of whether the light-emitting element has deteriorated can also be used to infer the cause of deterioration of the light emitting and receiving apparatus. If the light emitting and receiving apparatus includes a light-emitting element and a light-receiving element, for example, it becomes possible to discern whether the element that has deteriorated is the light-emitting element or the light-receiving element. If the light emitting and receiving apparatus includes a light-emitting element, a light guide, and a light-receiving element, for example, it becomes possible to discern whether the cause of deterioration is deterioration of the light-emitting element or deterioration of one of the light guide and the light-receiving element. In other words, the user can gain an indicator for judging which component should be replaced during maintenance. This can reduce unnecessary component replacement.

<First Modification>

Figure 3:
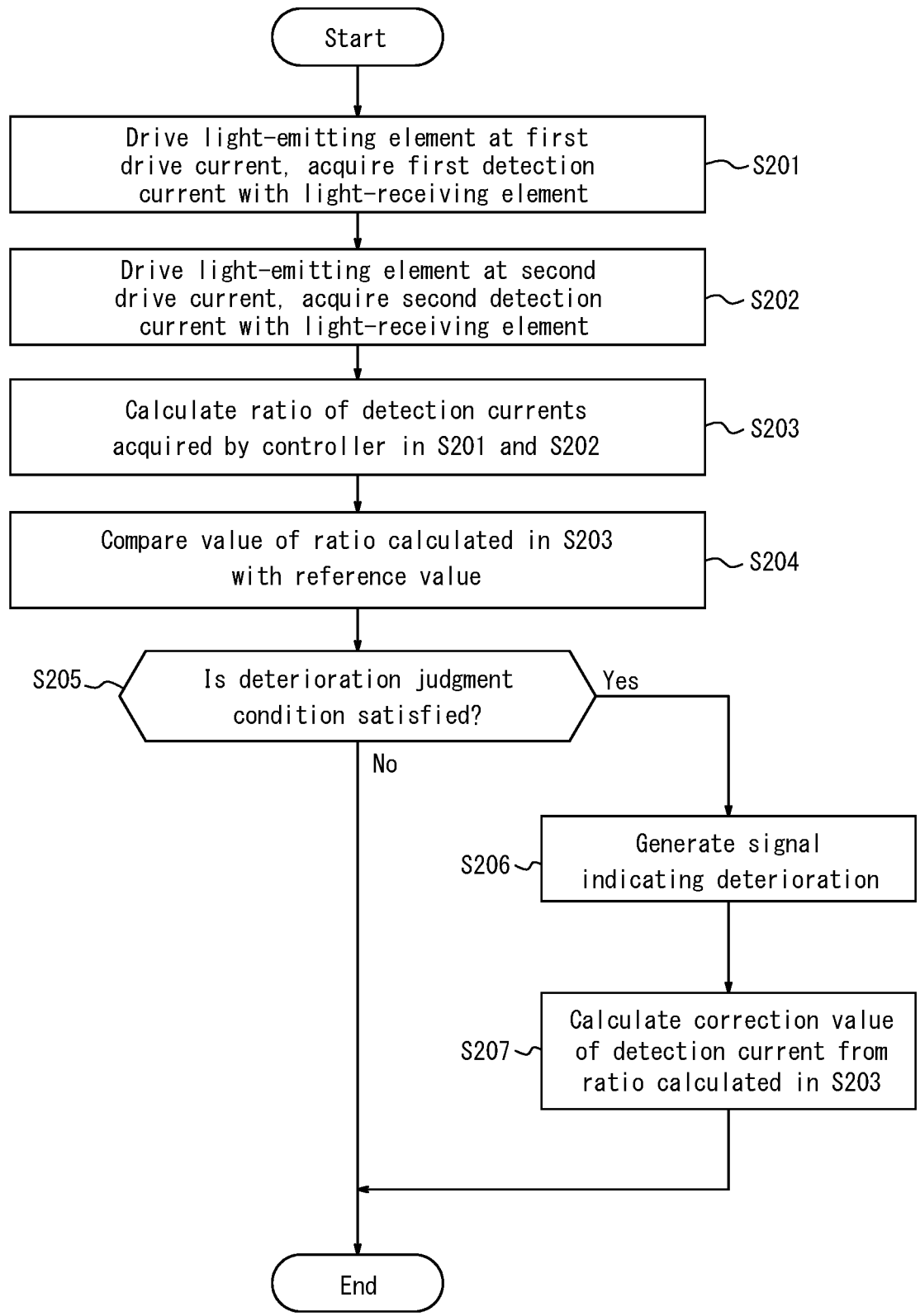
FIG. 3 is a flowchart illustrating an example of a method of diagnosing deterioration according to a first modification.

A method of diagnosing deterioration according to a first modification is now described with reference to FIG. 3. FIG. 3 is a flowchart illustrating an example of a method of diagnosing deterioration.

In step S201, the controller 30 drives the light-emitting element 10 at the first drive current and acquires the first detection current from the light-receiving element 20.

In step S202, the controller 30 drives the light-emitting element 10 at the second drive current and acquires the second detection current from the light-receiving element 20.

In step S203, the calculator 40 calculates the aging value, which is the ratio between the first detection current acquired in step S201 and the second detection current acquired in step S202.

In step S204, the calculator 40 calculates the ratio between a reference value and the aging value calculated in step S203 and compares this ratio with the threshold T. The threshold T is a predetermined value set by the user.

In step S205, the calculator 40 judges whether the ratio between the reference value and the aging value is greater than the threshold T, i.e. whether the deterioration judgment condition is satisfied. When the calculator 40 judges that the ratio between the reference value and the aging value is greater than the threshold T, i.e. that the deterioration judgment condition is satisfied, the process proceeds to step S206. When the calculator 40 judges that the ratio between the reference value and the aging value is equal to or less than the threshold T, i.e. that the deterioration judgment condition is not satisfied, the process terminates.

In step S206, the calculator 40 generates a signal indicating deterioration. And the calculator 40 may outputs an instruction signal to the communication interface 60.

In step S207, the calculator 40 uses the aging value calculated in step S203 to calculate a correction value for at least one of the first detection current and the second detection current. Specifically, the calculator 40 refers to a model, formulated in advance, of the deterioration correction value relative to the aging value to calculate a correction value for at least one of the first detection current and the second detection current. Here, the correction value may be calculated by a method of referring to a deterioration correction value quantified in advance relative to the aging value.

The method of diagnosing deterioration according to the first modification can easily and accurately diagnose the deterioration of a light-emitting element.

<Second Modification>

Figure 4:
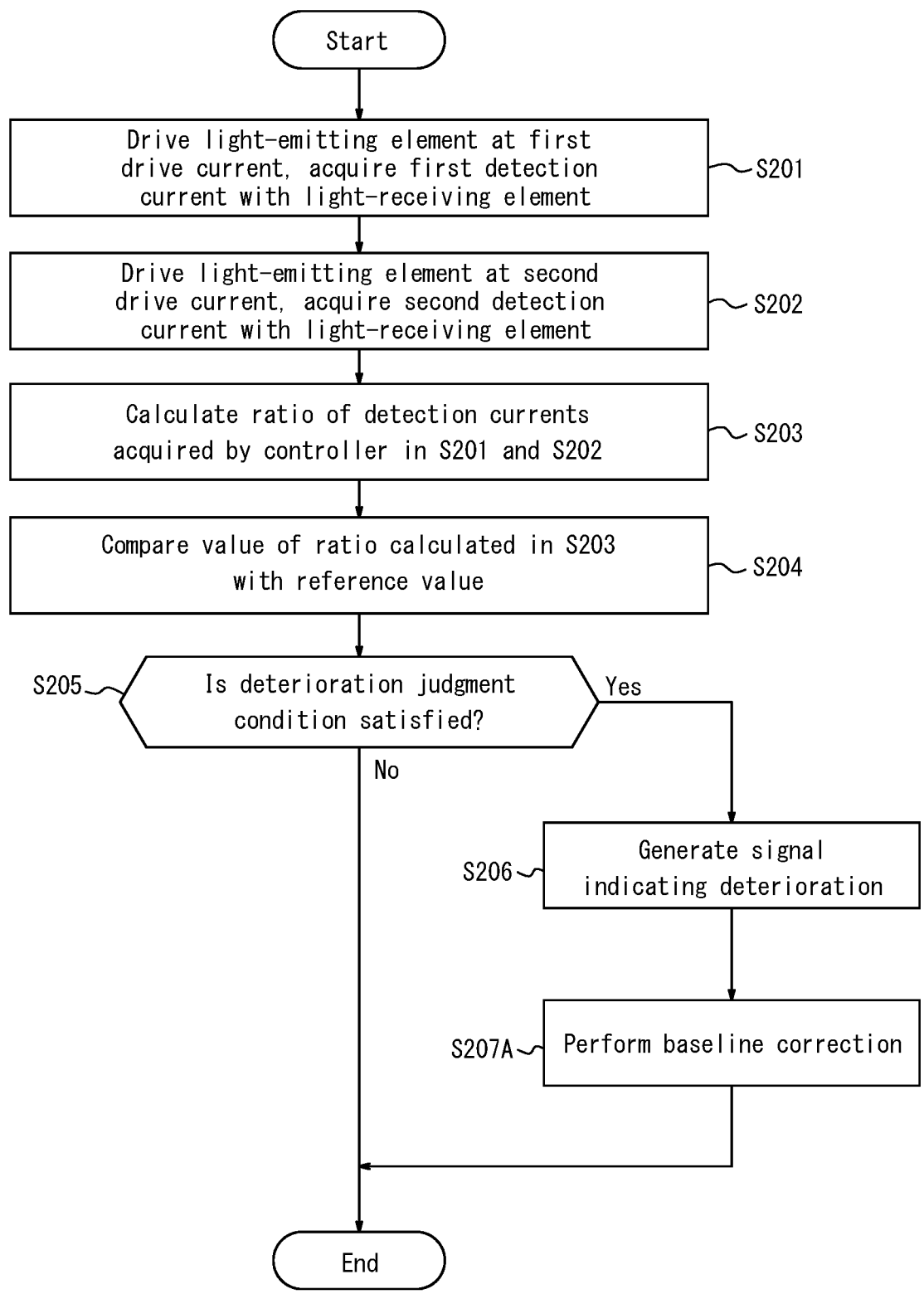
FIG. 4 is a flowchart illustrating an example of a method of diagnosing deterioration according to a second modification.

A method of diagnosing deterioration according to a second modification is now described with reference to FIG. 4. FIG. 4 is a flowchart illustrating an example of a method of diagnosing deterioration.

In step S201, the controller 30 drives the light-emitting element 10 at the first drive current and acquires the first detection current from the light-receiving element 20.

In step S202, the controller 30 drives the light-emitting element 10 at the second drive current and acquires the second detection current from the light-receiving element 20.

In step S203, the calculator 40 calculates the aging value, which is the ratio between the first detection current acquired in step S201 and the second detection current acquired in step S202.

In step S204, the calculator 40 calculates the ratio between a reference value and the aging value calculated in step S203 and compares this ratio with the threshold T. The threshold T is a predetermined value set by the user.

In step S205, the calculator 40 judges whether the ratio between the reference value and the aging value is greater than the threshold T, i.e. whether the deterioration judgment condition is satisfied. When the calculator 40 judges that the ratio between the reference value and the aging value is greater than the threshold T, i.e. that the deterioration judgment condition is satisfied, the process proceeds to step S206. When the calculator 40 judges that the ratio between the reference value and the aging value is equal to or less than the threshold T, i.e. that the deterioration judgment condition is not satisfied, the process terminates.

In step S206, the calculator 40 generates a signal indicating deterioration. And the calculator 40 may outputs an instruction signal to the communication interface 60.

In step S207A, the calculator 40 performs baseline correction. Specifically, this baseline correction is performed by referring to a model, formulated in advance, of the deterioration correction value relative to the threshold T and using the obtained deterioration correction value to correct all subsequent detection currents.

The method of diagnosing deterioration according to the second modification can easily and accurately diagnose the deterioration of a light-emitting element.

<Third Modification>

A method of diagnosing deterioration according to a third modification is now described with reference to FIG. 5. FIG. 5 is a flowchart illustrating an example of a method of diagnosing deterioration.

In step S201, the controller 30 drives the light-emitting element 10 at the first drive current and acquires the first detection current from the light-receiving element 20.

In step S202, the controller 30 drives the light-emitting element 10 at the second drive current and acquires the second detection current from the light-receiving element 20.

In step S203, the calculator 40 calculates the aging value, which is the ratio between the first detection current acquired in step S201 and the second detection current acquired in step S202.

In step S204, the calculator 40 calculates the ratio between a reference value and the aging value calculated in step S203 and compares this ratio with the threshold T. The threshold T is a predetermined value set by the user.

In step S205, the calculator 40 judges whether the ratio between the reference value and the aging value is greater than the threshold T, i.e. whether the deterioration judgment condition is satisfied. When the calculator 40 judges that the ratio between the reference value and the aging value is greater than the threshold T, i.e. that the deterioration judgment condition is satisfied, the process proceeds to step S206. When the calculator 40 judges that the ratio between the reference value and the aging value is equal to or less than the threshold T, i.e. that the deterioration judgment condition is not satisfied, the process terminates.

In step S206, the calculator 40 generates a signal indicating deterioration. And the calculator 40 may outputs an instruction signal to the communication interface 60.

In step S207B, the controller 30 uses the aging value calculated in step S203 to adjust the first drive current and the second drive current.

The method of diagnosing deterioration according to the third modification can easily and accurately diagnose the deterioration of a light-emitting element.

<Application of Embodiments>

The light emitting and receiving apparatus according to the present embodiment can be applied to various devices, such as a gas sensor that is included in a building or measurement device to detect a particular gas concentration; a gas sensor mounted in a portable communication device such as a mobile phone or a smart phone, a gas sensor that is included in a form of transportation such as an automobile, car, or airplane to detect gas concentration, an apparatus for detecting components of the substance (such as water or a bodily fluid) flowing through a light path space between a light-emitting element and light-receiving element, a blood glucose concentration measurement apparatus, or the like.

<Other Modifications>

In the example described in the present embodiment, the controller 30 and the calculator 40 are configured separately, but these components may be combined.

The above embodiments have been described as representative examples, but it will be apparent to one of ordinary skill in the art that numerous modifications and replacements may be made within the spirit and scope of the present disclosure. Therefore, the present disclosure should not be interpreted as being restricted to the above embodiments. A variety of changes and modifications may be made without departing from the scope of the appended claims. For example, a plurality of the structural blocks indicated in the diagrams of the embodiments may be combined into one, or one structural block may be divided into multiple parts.

The invention claimed is:

1. A light emitting and receiving apparatus comprising:
a light-emitting element configured to output light of an amount corresponding to a drive current;
a light-receiving element configured to receive light from the light-emitting element and output a detection current corresponding to an amount of received light;
a controller configured to supply the drive current to the light-emitting element and acquire the detection current from the light-receiving element; and
a calculator;
wherein the controller is configured to
    acquire a first detection current from the light-receiving element when supplying a first drive current to the light-emitting element; and
    acquire a second detection current from the light-receiving element when supplying a second drive current to the light-emitting element;
wherein the calculator is configured to generate a signal indicating deterioration of the light-emitting element when a reference value and an aging value satisfy a deterioration judgment condition, the aging value being a ratio between the first detection current and the second detection current, and
wherein the deterioration judgment condition is that a ratio between the reference value and the aging value is greater than a first threshold, or the ratio between the reference value and the aging value is equal to or less than a second threshold.

2. The light emitting and receiving apparatus of claim 1, wherein the calculator is configured to
calculate a reference value that is a ratio between the first detection current and the second detection current at a predetermined timing; and
calculate the aging value after a predetermined period elapses from the predetermined timing.

3. The light emitting and receiving apparatus of claim 1, further comprising a storage configured to store the reference value.

4. The light emitting and receiving apparatus of claim 1, further comprising:
a communication interface configured to communicate with an apparatus for performing calibration;
wherein the calculator outputs the signal indicating deterioration of the light-emitting element to the communication interface.

5. The light emitting and receiving apparatus of claim 1, wherein the calculator is configured to calculate a correction value for at least one of the first detection current and the second detection current using the aging value when the deterioration judgment condition is satisfied.

6. The light emitting and receiving apparatus of claim 1, wherein the calculator is configured to perform baseline correction when the deterioration judgment condition is satisfied.

7. The light emitting and receiving apparatus of claim 1, wherein the controller is configured to adjust the first drive current and the second drive current using the aging value when the deterioration judgment condition is satisfied.

8. The light emitting and receiving apparatus of claim 1, wherein the light-emitting element is a light-emitting diode or a semiconductor laser.

9. The light emitting and receiving apparatus of claim 1, wherein the light-emitting element emits light of a wavelength longer than 0.7 μm.

10. The light emitting and receiving apparatus of claim 1, wherein the light-receiving element is a quantum sensor or a quantum infrared sensor.

11. The light emitting and receiving apparatus of claim 1, wherein the light-emitting element and the light-receiving element are formed on a same substrate.

12. A method of diagnosing deterioration of a light-emitting element, the method being performed by a light emitting and receiving apparatus comprising a light-emitting element configured to output light of an amount corresponding to a drive current and a light-receiving element configured to receive light from the light-emitting element and output a detection current corresponding to an amount of received light, the method comprising:

supplying the drive current to the light-emitting element and acquiring the detection current from the light-receiving element;

acquiring a first detection current from the light-receiving element when a first drive current is supplied to the light-emitting element;

acquiring a second detection current from the light-receiving element when a second drive current is supplied to the light-emitting element; and generating a signal indicating deterioration of the light-emitting element when a reference value and an aging value satisfy a deterioration judgment condition, the aging value being a ratio between the first detection current and the second detection current, wherein the deterioration judgment condition is that a ratio between the reference value and the aging value is greater than a first threshold, or the ratio between the reference value and the aging value is equal to or less than a second threshold.

13. The method of diagnosing deterioration of claim 12, further comprising calculating a correction value for at least one of the first detection current and the second detection current using the aging value when the deterioration judgment condition is satisfied.

14. The method of diagnosing deterioration of claim 12, further comprising performing baseline correction when the deterioration judgment condition is satisfied.

15. The method of diagnosing deterioration of claim 12, further comprising adjusting the first drive current and the second drive current using the aging value when the deterioration judgment condition is satisfied.

* * * * *